US00PP19562P2

(12) United States Plant Patent
Fleuren

(10) Patent No.: US PP19,562 P2
(45) Date of Patent: Dec. 9, 2008

(54) QUINCE PLANT NAMED 'ELINE'

(50) Latin Name: *Cydonia oblonga*
Varietal Denomination: Eline

(75) Inventor: Henricus Marie Gerardus Carolus Fleuren, Baarlo (NL)

(73) Assignee: Boomkwekerijen Henri Fleuren B.V., Baarlo (NL)

( * ) Notice: Subject to any disclaimer, the term of this patent is extended or adjusted under 35 U.S.C. 154(b) by 188 days.

(21) Appl. No.: 11/494,097

(22) Filed: Jul. 27, 2006

(51) Int. Cl.
*A01H 5/00* (2006.01)

(52) U.S. Cl. ..... Plt./179

(58) Field of Classification Search ..... Plt./179
See application file for complete search history.

(56) References Cited

PUBLICATIONS

UPOVROM Citation for 'Eline' as per QZ PBR 20040587; Mar. 24, 2004.*

* cited by examiner

*Primary Examiner*—Kent L Bell
(74) *Attorney, Agent, or Firm*—C. A. Whealy

(57) ABSTRACT

A new and distinct cultivar of Quince plant named 'Eline', characterized by its upright plant habit; compatibility as a rootstock with all pear cultivars known to the Inventor; and frost tolerance.

2 Drawing Sheets

Botanical designation: *Cydonia oblonga.*
Cultivar denomination: 'Eline'.

BACKGROUND OF THE INVENTION

The present invention relates to a new and distinct cultivar of Quince, typically used as a rootstock, botanically known as *Cydonia oblonga* and hereinafter referred to by the name 'Eline'.

The new Quince is a product of a planned breeding program conducted by the Inventor in Baarlo, The Netherlands. The objective of the breeding program was to develop new rootstock Quince cultivars with frost tolerance.

The new Quince originated from a cross-pollination made by the Inventor in April, 1991 of two unnamed seedling selections of *Cydonia oblonga)* not patented. The new Quince was discovered and selected by the Inventor from within the progeny of the stated cross-pollination in a controlled environment in Baarlo, The Netherlands in October, 1994.

Asexual reproduction of the new Quince by cuttings in a controlled environment in Baarlo, The Netherlands since April, 1995, has shown that the unique features of this new Quince are stable and reproduced true to type in successive generations.

SUMMARY OF THE INVENTION

The cultivar Eline has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Eline'. These characteristics in combination distinguish 'Eline' as a new and distinct cultivar of Quince:

1. Upright plant habit.
2. Compatible as a rootstock with all pear cultivars known to the Inventor.
3. Frost tolerance.

Plants of the new Quince differ from plants of the parent selections primarily in frost tolerance as plants of the parent selections are not frost tolerant.

Plants of the new Quince can also be compared to plants of the cultivar Quince-A, not patented. Plants of the new Quince differ from plants of the cultivar Quince-A in the following characteristics:

1. Plants of the new Quince are more erect than plants of the cultivar Quince-A.
2. Plants of the new Quince are more frost tolerant than plants of the cultivar Quince-A.

BRIEF DESCRIPTION OF THE PHOTOGRAPHS

The accompanying colored photographs illustrate the overall appearance of the new Quince, showing the colors as true as it is reasonably possible to obtain in colored reproductions of this type. Colors in the photographs may differ slightly from the color values cited in the detailed botanical description which accurately describe the colors of the new Quince.

The photograph on the first sheet comprises a side perspective view of typical plants of 'Eline' grown in an outdoor nursery.

The photograph on the second sheet is a close-up view of a typical plant of 'Eline'.

DETAILED BOTANICAL DESCRIPTION

The aforementioned photographs and following observations, measurements and values describe plants grown in Baarlo, The Netherlands, under commercial practice in an outdoor nursery. Plants were grown for about two years when the photographs and description were taken. In the following description, color references are made to The Royal Horticultural Society Colour Chart, 2001 Edition, except where general terms of ordinary dictionary significance are used.

BOTANICAL CLASSIFICATION: *Cydonia oblonga* cultivar Eline.

Parentage:

*Female, or seed, parent.*—Unnamed seedling selection of *Cydonia oblonga,* not patented.

*Male, or pollen parent.*—Unnamed seedling selection of *Cydonia oblonga,* not patented.

Propagation:

*Type.*—By cuttings.

*Time to initiate and develop roots.*—About five months.

*Root description.*—Fibrous; white to brown in color.

Plant description:

*Plant form/habit.*—Fruit tree rootstock; compatible with all pear cultivars known to the Inventor. Upright habit; narrow inverted triangle. When pruned, about five to six lateral branches develop. Moderately vigorous.

*Plant height.*—About 80 cm to 1 meter.

*Plant width* (*spread*).—About 60 cm to 80 cm.

*Lateral branches.*—Length: About 60 cm to 80 cm. Diameter: About 5 mm to 1 cm. Internode length: About 2 cm to 3 cm. Strength: Strong. Texture: Smooth, glabrous. Color: 197A.

Foliage description:

*Arrangement.*—Alternate, simple.

*Length.*—About 5 cm to 6 cm.

*Width.*—About 3 cm to 3.5 cm.

*Shape.*—Ovate.

*Apex.*—Acute.

*Base.*—Cordate.

*Margin.*—Entire.

*Texture, upper surface.*—Smooth, glabrous.

*Texture, lower surface.*—Pubescent.

*Venation pattern.*—Pinnate.

Color. —Developing and fully developed leaves, upper surface: 143A; venation, 144A. Developing and fully developed leaves, lower surface: 143B; venation, 146B.

*Petiole.*—Length: About 8 mm to 1 cm. Diameter: About 2 mm. Texture, upper and lower surfaces: Smooth, glabrous. Color, upper and lower surfaces: 174A.

Flower description: Flower initiation and development has not been observed on plants of the new Quince.

Disease/pest resistance: Plants of the new Quince have not been noted to be resistant to pathogens and pests common to Quince.

Temperature tolerance: Plants of the new Quince are frost tolerant and have been observed to tolerate temperatures from −25° C. to 35° C.

It is claimed:

1. A new and distinct Quince plant named 'Eline' as illustrated and described.

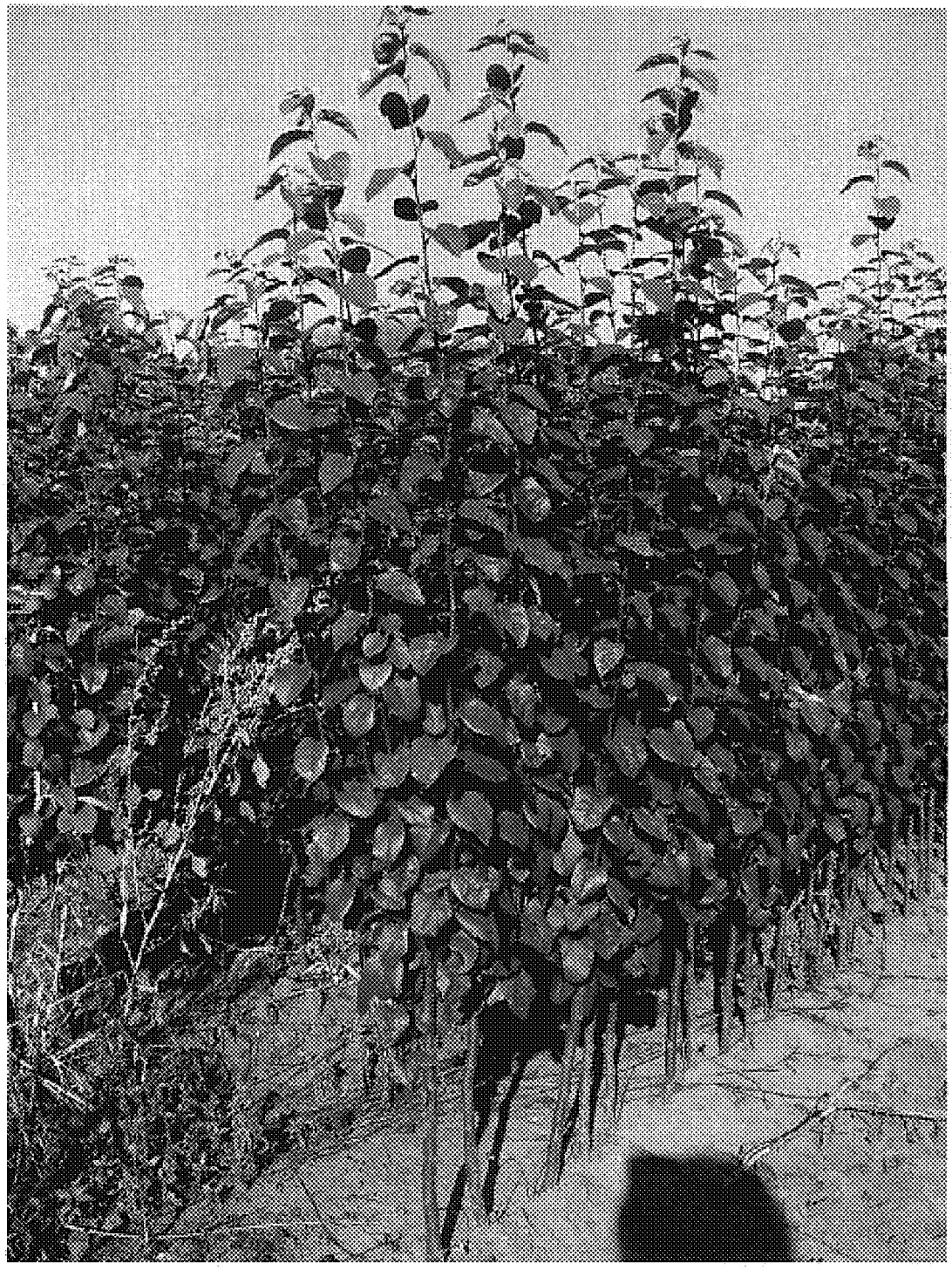

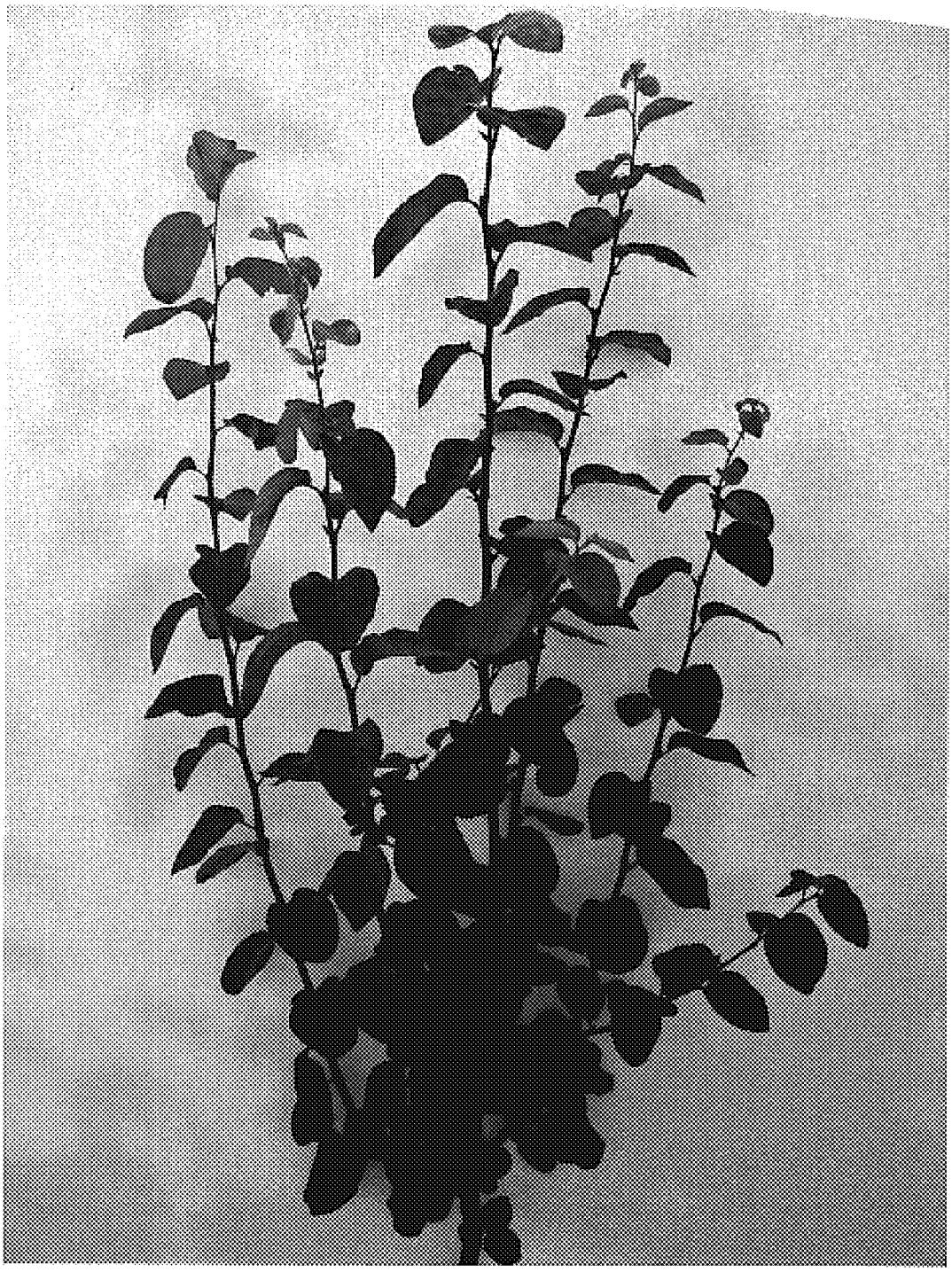

* * * * *